United States Patent [19]

Jaeger

[11] Patent Number: 4,744,255
[45] Date of Patent: May 17, 1988

[54] SAMPLER AND METERING PUMP

[76] Inventor: Ben E. Jaeger, 50 Hunter La., Plano, Ill. 60545

[21] Appl. No.: 29,202

[22] Filed: Mar. 23, 1987

[51] Int. Cl.$^4$ ............................................. G01N 1/14
[52] U.S. Cl. ................................. 73/863.84; 222/275; 73/863.82
[58] Field of Search ............ 73/863.82, 863.83, 863.84

[56] References Cited

U.S. PATENT DOCUMENTS

| | | |
|---|---|---|
| 3,218,868 | 11/1965 | Gill . |
| 3,681,996 | 8/1972 | Crist . |
| 4,269,064 | 5/1981 | Johnson et al. ................. 73/863.84 |
| 4,475,410 | 10/1984 | Jaeger ............................ 73/863.84 |
| 4,479,393 | 10/1984 | Shores ............................ 73/863.82 |

Primary Examiner—Tom Noland
Attorney, Agent, or Firm—Juettner Pyle Lloyd & Verbeck

[57] ABSTRACT

A sampler for communicating with the interior of a vessel containing a liquid extracts a liquid sample of predetermined volume from the vessel and conveys the same to a point of collection. The sampler includes a body having a bore, the forward end of which is in communication with the interior of the vessel, along with front and rear plungers reciprocable within the bore under positive independent control. The plungers are movable away from and toward each other to establish and collapse a sample chamber therebetween. To obtain a liquid sample, the plungers are removed forwardly to project the front plunger out of the bore and place the sample chamber into communication with the vessel interior, whereupon the sample chamber is established for being filled with liquid. The plungers are then moved rearwardly into the bore with the liquid filled sample chamber therebetween, until the chamber is exposed to a port in the bore, at which point it is collapsed to force the liquid out of the chamber and through the port under positive pressure. The sampler may also be used as a metering pump, with liquid being introduced into the sample chamber through the port and then carried through the bore by the plungers to and into the vessel.

17 Claims, 3 Drawing Sheets

SAMPLER AND METERING PUMP

BACKGROUND OF THE INVENTION

The present invention relates to apparatus for extracting or adding measure volumes of liquid from or to flow lines or tanks.

Various manufacturing operations require that the immediate or overall composition of a liquid flowing through a pipe be monitored. Such monitoring ordinarily is accomplished with apparatus denoted as samplers, which take samples of liquid from a main body thereof. Where a composite sample of the liquid is required, the sampler may be operated to withdraw a series of small, measured amounts of the liquid as it passes a sampling point. The small, measured amounts are collected, and form a representative, composite sample of the total volume of liquid.

Other uses for samplers are in on-line analysis applications, in which the immediate composition of a liquid must be determined. For this application, the individual samples of liquid are not collected as a composite sample, but instead are analyzed separately.

To obtain samples, some samplers continuously divert streams of liquid from the flow lines or tanks, and from the diverted streams, the samples are removed in various ways. Attempts to withdraw small, measured quantities directly from the pipes or tanks, however, have presented many problems not altogether satisfactorily solved. For example, where liquid receiving holes or slots are extended directly into a pipe, the sampler often requires an orienting mechanism, and the sampled material can build up in such holes and slots and either block the same or contaminate subsequent samples. In addition, conventional samplers often are difficult to disassemble for inspection, cleaning and replacement of parts, and excessive leakage and clogging are problems common to many types of samplers.

Heretofore, samplers of the general type have been used to obtain samples of relatively nonviscous liquids. In recent years, a need has arisen to sample liquids which are viscous, for example catsup, mayonnaise, juice concentrate, toothpaste and heavy grease. Conventional samplers do not perform satisfactorily when used to sample such highly viscous liquids, since the sampled material is too thick to effectively flow into and then off and out of the sampler for collection. Two types of samplers adapted to handle relatively viscous materials are taught by Johnson et al U.S. Pat. No. 4,269,064, and by my U.S. Pat. No. 4,475,410, each of which defines a sample chamber between two members that may be moved together to collapse the chamber and eject the sample under positive pressure. However, each sampler is somewhat limited in versatility because of a lack of positive independent control over movement of the two members.

In addition to extracting measured samples of liquid, it often is necessary to meter measured volumes of liquid into lines or tanks. For such situations, it would be advantageous if the same apparatus used to extract samples could also be used as a metering pump to add measured volumes of liquid to the line or tank.

OBJECTS OF THE INVENTION

An object of the invention is to provide a sampler for withdrawing measured samples of liquid from a vessel.

Another object is to provide a sampler for extracting samples of relatively viscous liquids.

A further object is to provide a sampler that ejects the sample under positive pressure at a collection point, and which is suited for automatic operation at selected intervals.

A yet further object is to provide a sampler having a sample chamber which may selectively be established and collapsed, which establishes the chamber while within the vessel to prevent contamination of the contents of the vessel, and then carries the sample in the chamber to a collection point.

Yet another object is to provide a sampler which may also be operated as a metering pump to inject measured volumes of liquid into the vessel.

SUMMARY OF THE INVENTION

In accordance with the present invention, apparatus adapted to be mounted on a vessel containing a liquid comprises a housing having a bore for communication at a forward end with the interior of the vessel. A front plunger is reciprocable in the bore between positions within and sealed with the bore, and forwardly out of the bore to extend the plunger at least partially into the interior of the vessel, and a rear plunger is reciprocable within and sealed with the bore immediately rearwardly of the front plunger. The front and rear plungers are movable to a spaced apart relationship to establish a space therebetween, and into abutting relationship to collapse the space, and a port extends through the housing into communication with the bore. Also included is drive means for independently reciprocating the plungers either forwardly or rearwardly. The drive means moves the plungers to positions where the rear plunger is forwardly in the bore, the front plunger is out of the forward end of the bore and at least partially into the vessel, and the space is in communication with the interior of the vessel. The drive means also moves the plungers to positions where the rear plunger is rearwardly in the bore, the front plunger is moved rearwardly into the bore, and the space is in the bore in communication with the port.

According to one embodiment, the space comprises a collapsible chamber defined by opposing faces of the front and rear plungers and the inner wall of the bore when the plungers are within the bore, and the chamber has a predetermined volume when the plungers are in spaced apart relationship. In this case, the drive means moves the plungers forwardly to positions where the front plunger is out of the bore and the chamber is established and in communication with the interior of the vessel for being filled with liquid. It then simultaneously moves the plungers rearwardly to bring the front plunger into the bore with the liquid filled chamber between the plungers, and to thereafter position the chamber in communication with the port. It then moves the plungers into abutting relationship to collapse the chamber and eject the liquid therein through the port under positive pressure. In this manner, the apparatus obtains a liquid sample of predetermined volume from the vessel and conveys the sample to and through the port.

According to another embodiment, the port is for communicating with a source of liquid additive. In this case, starting with the plungers in their rearward positions in the bore, and with the chamber collapsed and in communication with the port, the drive means moves the plungers apart to establish the chamber and fill the same with additive through the port. It then moves the plungers forwardly with the additive filled chamber therebetween, to a position where the front plunger is out of the forward end of the bore and the chamber is in communication with the vessel interior. Next, it moves the plungers into abutting relationship to collapse the chamber and positively eject the additive into the vessel and, finally, it moves the plungers rearwardly to bring the front plunger into the bore and to return the collapsed chamber into communication with the port. In this manner, the apparatus operates as a metering pump to inject a predetermined volume of additive into the vessel.

The foregoing and other objects, advantages and features of the invention will become apparent upon a consideration of the following detailed description, when taken in conjunction with the accompanying drawings.

DETAILED DESCRIPTION

Figure 1:
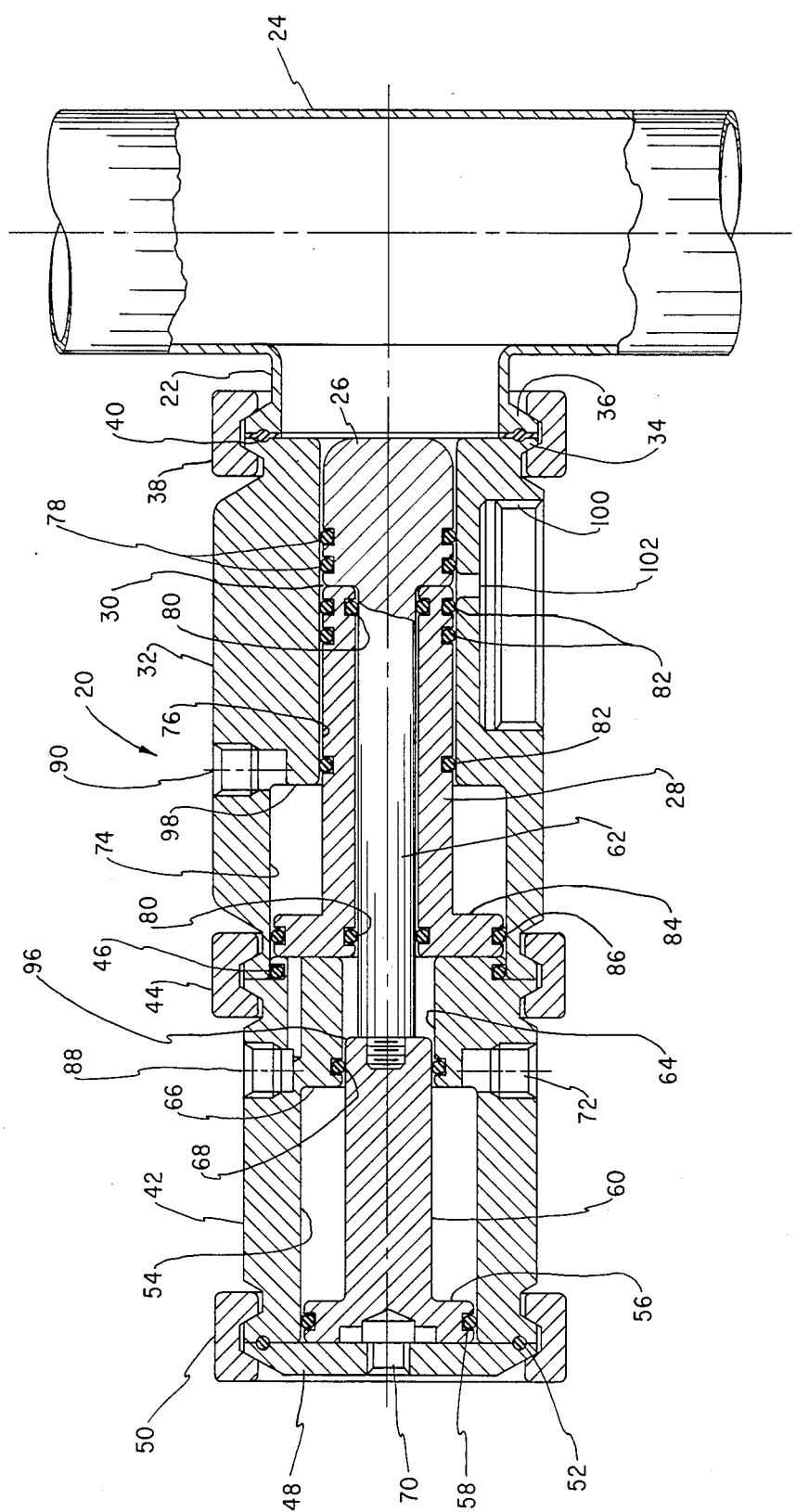
FIG. 1 is a cross sectional, side elevation view of a sampler according to the teachings of the invention, showing front and rear plungers of the sampler in retracted positions whereat a sampling chamber between the plungers is collapsed.

Referring to the drawings, there is indicated generally at 20 a sampler structured in accordance with a preferred embodiment of the invention. The sampler is adapted for connection with an access line 22 to a conduit 24, in which is conveyed liquid materials that may be relatively viscous and include, by way of example, catsup, mayonnaise, juice concentrate, toothpaste and heavy grease. The sampler has front and rear plungers 26 and 28 that are independently movable under positive control, and which may be moved apart to define a sample chamber 30 between their facing ends, and together to collapse the chamber. The plungers are movable toward the conduit to positions where the sample chamber is established between the plungers and in communication with the vessel interior, and the front plunger 26 is at least partially extended into the conduit, for filling of the chamber with liquid from the vessel. The plungers are also then movable away from the conduit to convey the sample in the chamber to a collection point, where the plungers are brought together to collapse the sample chamber and eject the sample from the chamber under positive pressure. The sampler may be cyclically actuated, so that the sampler may be cyclically actuated, so that the collected material forms a representative, composite sample of material flowing through the conduit, and a plurality of seals maintain liquid seals between the interior of the conduit and collection point and between the collection point and motor means. Further, and as will be described, in addition to being operable to perform a sampling function, the device may also be operated as a metering pump, to inject measured volumes of liquid additive into the conduit.

More particularly, the outer portion of the sampler 20 includes a body 32 having a flange 34 at its forward end, which connects with a flange 36 on the access line 22 by means of a quick release clamp 38, and a seal 40 establishes a fluid tight connection between the flanges. A pneumatic drive cylinder 42 connects at its forward end with the rearward end of the body 32 by means of a quick release clamp 44, and a seal 46 is between the drive cylinder and body. An end plate 48 is held on the rearward end of the cylinder by a quick release clamp 50, and a seal 52 is between the plate and cylinder.

A first motor means, for moving the front plunger 26, includes the cylinder 42 in which is defined a cylinder passage 54. A piston 56 in the passage is slidingly sealed therewith by a seal 58, and a piston rod, having a rearward portion 60 of a first diameter, and a forward portion 62 of a second and smaller diameter, connects with the piston and extends forwardly through a reduced diameter passage 64 in the cylinder, defined forwardly of a radially inwardly extending shoulder 66. The piston rod portion 60 is slidingly sealed with the passage 64 by an annular seal 68, and to reciprocate the piston rod, an air inlet or port 70 in the end plate 48 communicates with the rearward end of the cylinder passage 54, and an air inlet or port 72 in the cylinder 42 communicates with the forward end of the passage. Introduction of air at the inlet 70 moves the piston and piston rod rightwardly (as shown in the drawings), and introduction of air at the port 72 moves the piston and piston rod leftwardly.

The sampling portion of the device 20 includes the body 32, in which is defined both a rearward cylinder passage 74 of a first diameter, and a forward bore 76 of a second and smaller diameter, the bore also having a diameter smaller than that of the access line 22. The front plunger 26 is slidably sealed with the bore by a pair of annular seals 78, and is carried on the forward end of the piston rod portion 62.

The rear plunger 28 comprises a tubular member slidably disposed about the piston rod 62 rearwardly of the front plunger 26, and a pair of seals 80 form a fluid tight connection between the rear plunger and piston rod. The rear plunger also is reciprocable within the bore 76, it is sealed therewith by seals 82, and a second motor means, for reciprocating the rear plunger, includes the cylinder passage 74 in the body 32. A piston 84 in the passage is slidingly sealed therewith by a seal 86, and the piston connects with the rearward end of the rear plunger. To reciprocate the rear plunger, an air inlet or port 88, in the cylinder 42, communicates with a rearward end of the cylinder passage, and a port 90 in the body communicates with a forward end of the passage. Introduction of air at the inlet 88 moves the piston and rear plunger rightwardly (as shown in the drawings), and introduction of air at the inlet 90 moves the piston and rear plunger leftwardly.

Figure 2:
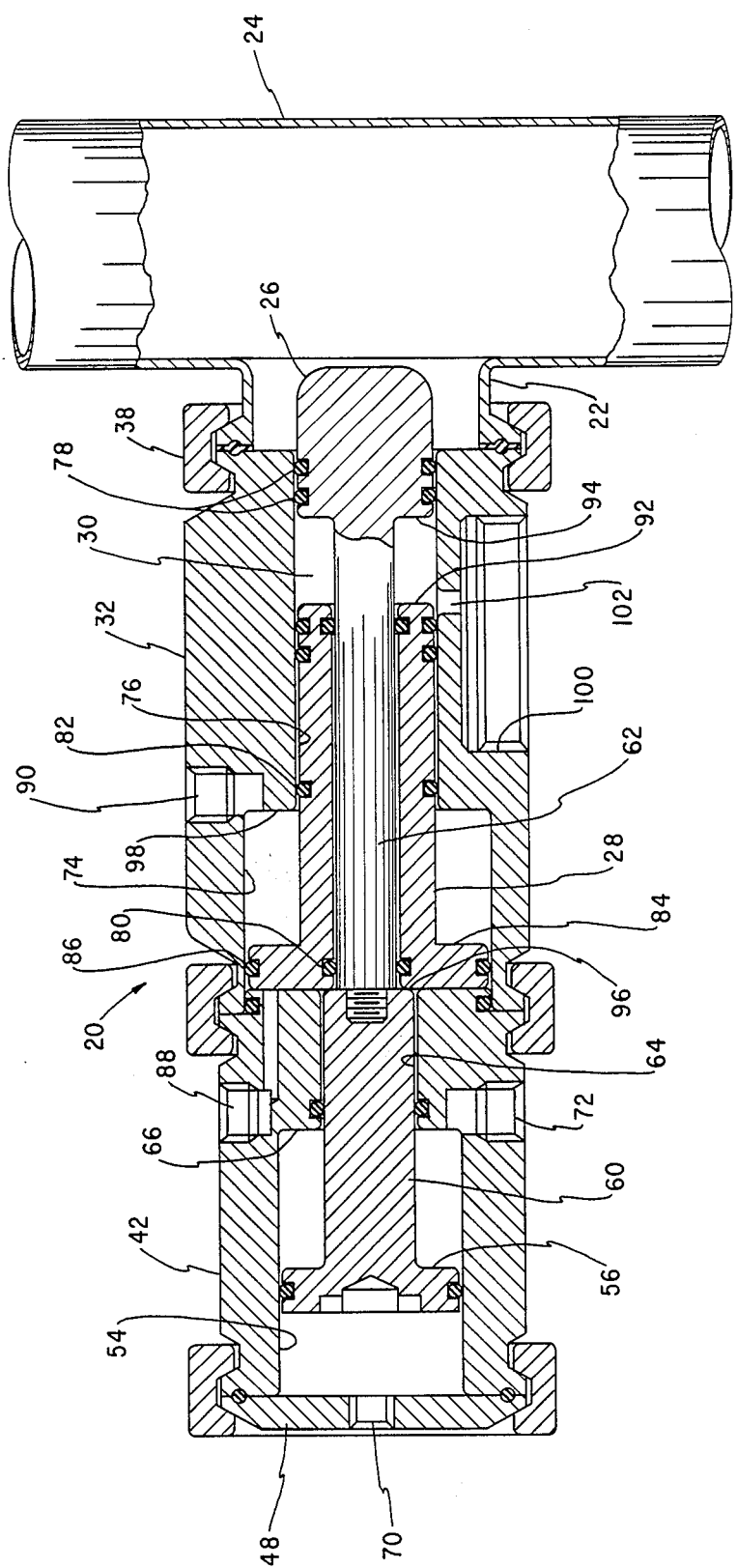
FIG. 2 is similar to FIG. 1, except that the front and rear plungers are spaced apart to define the sampling chamber between the plungers.
Figure 3:
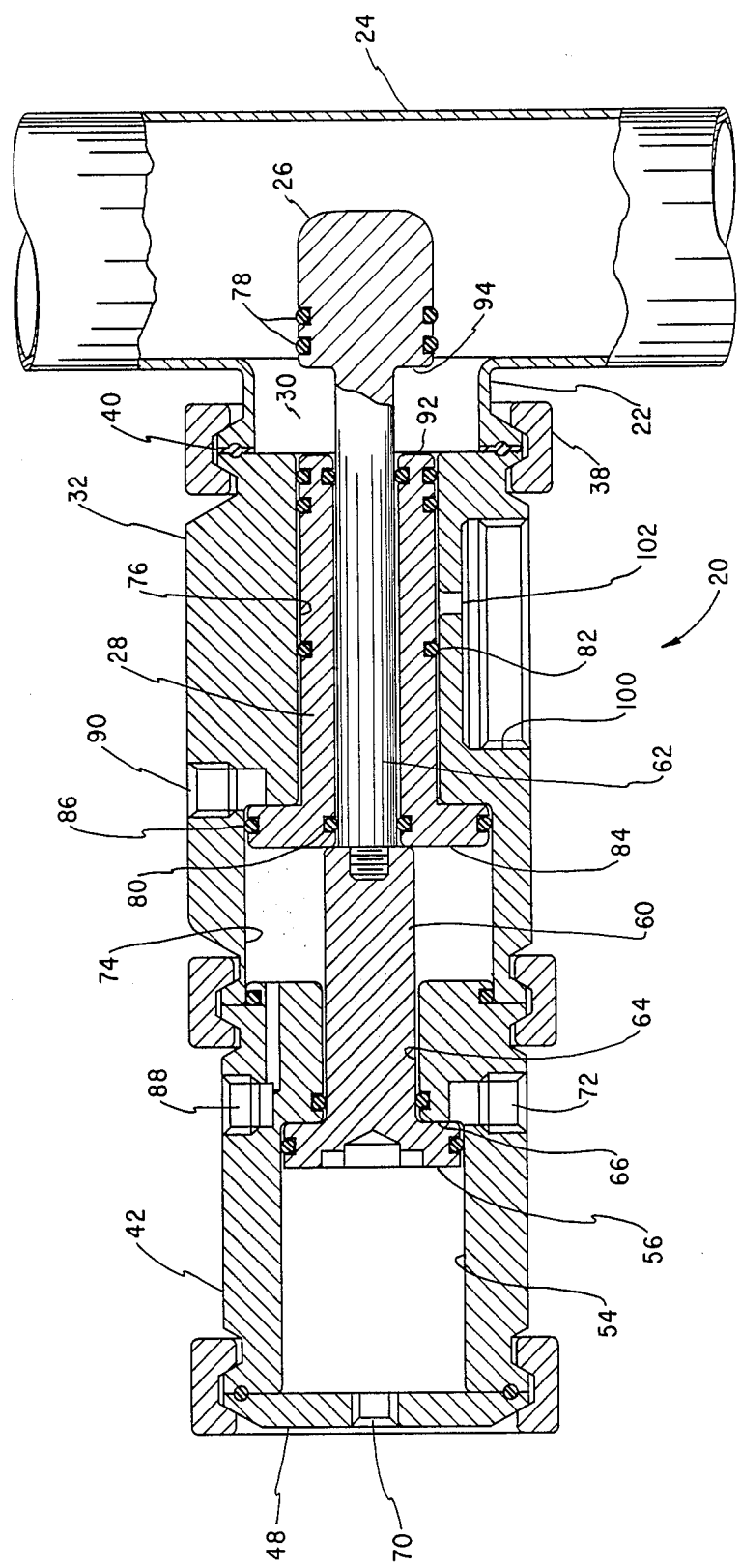
FIG. 3 is similar to FIG. 2, except that the front and rear plungers have been moved forwardly to place the sampling chamber in communication with the interior of a conduit.

The sample chamber 30 is defined between a front face 92 of the rear plunger 28, a rear face 94 of the front plunger 96, the piston rod portion 62 and the surrounding surface of the bore 76. The lengths of the piston rod portions 60 and 62, the rear plunger 28 and the pistons 56 and 84, are selected so that, with the pistons in their leftwardmost positions as shown in FIG. 1, with at least the piston 84 abutting the rearward end of its cylinder passage 74, the opposing faces of the plungers are abutting and the sample chamber is collapsed. The lengths are also chosen so that, upon rightward movement of the piston 56, and engagement of a shoulder 96 between the piston rod portions 60 and 62 with the rearward end of the piston 84, the front plunger is moved to a predetermined spaced relationship from the rear plunger, so that the sample chamber has a selected volume (FIGS. 2 and 3). In addition, the lengths of the cylinder passages 54 and 74 are selected so that, with the shoulder 96 abutting the back side of the piston 84 and the piston abutting a shoulder 98 at the forward end of the passage 74, the front plunger is projected at least partially into the conduit 24, and the sample chamber is in communication with fluid in the conduit, at which time the piston 56 may either abut or be spaced from the shoulder 66 at the forward end of its cylinder passage 54.

The remainder of the device 20 comprises means for collecting liquid samples. To that end, the body 32 has an enlarged opening 100 within which a container (not shown) for receiving and storing liquid samples may be attached, for example by being threaded into the opening. Extending between the opening and bore 76 is a discharge port or orifice 102, which enters the bore at a point such that the front face 92 of the rear plunger 28 overlies the port when the plunger is in its leftmost position.

In a quiescent state, and prior to initiation of a sampling operation, air under pressure is applied at the ports 72 and 90, while the ports 70 and 88 are vented, to maintain the pistons 56 and 84 in their leftmost positions, and the rear and front plungers 28 and 26 fully retracted and abutting within the bore 76, so that as shown in FIG. 1, the sample chamber or annulus 30 is collapsed. To initiate a sampling operation, air under pressure is applied at the port 88, while the ports 70, 72 and 90 are vented, to drive the piston 84 rightwardly to move the rear plunger, along with the front plunger which is pushed by the rear plunger, forwardly through the bore with the sample chamber closed, until the piston abuts the shoulder 98. At this point, the sample chamber, although closed, is in communication with the interior of the vessel, the front plunger is projected out of the bore, and air under pressure is also connected with the port 70 to drive the piston 56 rightwardly. This moves the front plunger further forwardly and away from the rear plunger, to establish the sample chamber and extend the front plunger at least partially into the conduit, until the shoulder 96 on the piston rod portion 60 engages the piston 84.

The maximum forward extension of the front plunger 26 into the conduit 24 is shown in FIG. 3. At this point, the plunger is projected out of the bore 76 and at least partially into the conduit, is spaced from the rear plunger 28 to fully open the sample chamber 30, and the sample chamber is in communication with the conduit interior. Because the rear plunger is moved fully forward with the sample chamber closed before the front plunger is moved away from it to establish the chamber, the sample chamber is placed into communication with the conduit interior while it is collapsed. Consequently, contamination of the liquid in the conduit is avoided, since virtually no air or liquid may be carried forward in the sample chamber from the region of the discharge port 102. Instead, liquid in the conduit is "sucked" into the sample chamber as it is opened by movement of the front plunger away from the rear plunger.

After the sample chamber 30 has been at least momentarily established, air under pressure is connected to the port 90, the ports 72 and 88 are vented, and the port 70 is either vented through a restrictor (not shown), or connected to a source of air at a reduced pressure. This causes the piston 84 to move leftwardly and carry with it, by engagement with the shoulder 96 of the piston rod portion 60, the piston 56, to move the rear plunger 28 rearwardly through the bore 76 and retract the front plunger 26 into the bore, with the fluid filled sample chamber therebetween, until the piston 84 engages the rearward end of the cylinder passage 74. At this point, the front face 92 of the rear plunger is at least partially over but not beyond the discharge port 102, and the sample chamber is in communication with the port. Air under pressure is then also applied at the port 72, and the port 70 is freely vented, to cause the front plunger to move toward and abut the rear plunger to collapse the sample chamber and eject the liquid in the chamber through the discharge port under positive pressure, whereupon the sampling cycle is completed.

The invention thus provides an improved sampler for liquid materials, particularly relatively viscous liquid materials. By virtue of the independent and positive pneumatic control over movement of each of the front and rear plungers 26 and 28, the sample chamber 30 may be maintained collapsed while it is moved into communication with the conduit interior, so that a significant amount of air or gas from the region of sample discharge cannot be carried into the conduit. Also, by extending the sample chamber into communication with the product stream in the closed condition, and then opening or establishing the chamber, even high viscosity products are readily "sucked" or drawn into the chamber. The arrangement is especially useful in sampling products that are static in a tank and/or at zero or negative atmospheric pressure. Further, the positive pneumatic control allows sampled material to be forced through a lengthy discharge tube, with the sampler acting as a force pump during sample discharge. It is to be appreciated, of course, that if desired the sample chamber could be opened at the beginning of a sampling cycle, while in communication with the discharge port, simply by initially connecting air under pressure to each of the ports 70 and 90.

The invention also contemplates a rearrangement of the port program of the device 20, that permits it to be used to introduce small quantities of a liquid additive into the conduit. In other words, it may be used as a "meter-in" pump, as compared with a "meter-out" sampler.

In the arrangement of the device 20 for operation as a metering pump, the discharge port 102 serves as an inlet to the device, and is connected to a supply of liquid additive to be metered into the conduit 24. In a quiescent state of the pump and prior to initiation of a metering cycle, air under pressure is connected to the ports 72 and 90, while the ports 70 and 88 are vented, to maintain the front and rear plunger 26 and 28 in their retracted positions and the chamber 30 closed.

At the beginning of a metering cycle, air under pressure is connected to the ports 70 and 90, while the ports 72 and 88 are vented, to move the front plunger 26 forwardly, while maintaining the rear plunger 28 stationary, to open the chamber 30. As the chamber is opened, a negative pressure is generated within it, which draws additive through the port 102 and into the chamber, until it is fully opened and filled with additive. Then, while air under pressure continues to be connected to the port 70, all of the ports 72, 80 and 90 are vented, so that the piston 56 moves the front and rear plungers, together with the additive filled chamber therebetween, forwardly through the bore 76, until the front plunger moves out of the bore and the chamber is placed in communication with the conduit interior. The chamber is then closed, to positively eject the additive into the conduit, by connecting air under pressure to the ports 72 and 88, while venting the ports 70 and 90, to retract the front plunger into engagement with the rear plunger. Collapsing the chamber while within the conduit also ensures that, in a next step, a significant volume of product from the conduit will not be carried by the chamber to the port 102.

Lastly, the front and rear plungers 26 and 28 are retracted by continuing to apply air under pressure to the port 72, while venting all of the ports 70, 88 and 90, until the piston 84 engages the rearward end of its cylinder passage 74. Air under pressure is then applied to both of the ports 72 and 90, while the ports 70 and 88 are vented, to place the device in its quiescent state in preparation for the next cycle.

The invention therefore provides an improved apparatus, having a pair of plungers that are independently operable under positive control. The apparatus may readily be operated either as a meter-out sampler that obtains samples of material from a vessel and conveys the same to a collection point, or as a meter-in pump that injects measured volumes of an additive into a vessel. Also, at all times during operation of the apparatus, seals carried by the plungers maintain liquid seals between the conduit interior and collection point.

While embodiments of the invention have been described in detail, various modification and other embodiments thereof may be devised by one skilled in the art, without departing from the spirit and scope of the invention, as defined in the appended claims.

What is claimed is:

1. Apparatus adapted to be mounted on a vessel, said apparatus comprising a housing having a bore for communication at a forward end with the interior of the vessel; a front plunger reciprocable between positions within and sealed with said bore and forwardly completely out of said bore; a rear plunger reciprocable within and sealed with said bore immediately rearwardly of said front plunger, said front and rear plungers being reciprocable to a predetermined spaced apart relationship to establish a space therebetween and to abutting relationship to collapse said space; a port through said housing in communication with said bore; and drive means operatively connected to said plungers for independently reciprocating each of said plungers forwardly and rearwardly and for moving said plungers between positions whereat said rear plunger is moved forwardly in said bore, said front plunger is moved out of said forward end of said bore and said space is in communication with the interior of the vessel, and whereat said rear plunger is moved rearwardly in said bore, said front plunger is moved rearwardly into and in sealed relationship with said bore and said space is in said bore in communication with said port.

2. Apparatus as in claim 1, wherein said space, when established between said plungers, is an annular chamber of predetermined volume.

3. Apparatus as in claim 1, wherein said drive means comprises first and second motor means respectively operatively connected with said front and rear plungers for independently moving said plungers forwardly and rearwardly.

4. Apparatus as in claim 3, wherein said first and second motor means comprise first and second pneumatic drive means.

5. Apparatus as in claim 4, wherein each said pneumatic drive means comprises a piston in an associated cylinder passage having a pair of inlet ports, one for receiving fluid under pressure to operate the pneumatic drive means to move its associated plunger forwardly and the other for receiving fluid under pressure to operate the pneumatic drive means to move its associated plunger rearwardly.

6. Apparatus as in claim 1, wherein said apparatus is adapted to be mounted on a vessel containing a liquid material, said space comprises a collapsible chamber of predetermined volume defined by opposing faces of said front and rear plungers and the inner wall of said bore when said plungers are within said bore in said predetermined spaced apart relationship, and said drive means reciprocates said plungers forwardly to a position whereat said front plunger is out of said bore and said chamber is established and in communication with the interior of the vessel for being filled with liquid from the vessel, then rearwardly to a position whereat said front plunger is in said bore and said liquid filled chamber is between said plungers and in communication with said port, and then into abutting relationship to collapse said chamber and eject the liquid therein through said port under positive pressure, whereby said apparatus obtains a liquid sample of predetermined volume from the vessel and conveys the sample to and through said port.

7. Apparatus as in claim 6, wherein said drive means reciprocates said plungers forwardly in abutting relationship to initially place said chamber in communication with the vessel interior while said chamber is collapsed, and then moves said plungers to said predetermined spaced apart relationship to establish said chamber while said chamber is in communication with the vessel interior and prior to reciprocating said plungers rearwardly, whereby said chamber does not carry gas or liquid from the region of said port to the vessel interior and contamination of the liquid in the vessel is minimized.

8. Apparatus as in claim 7, wherein said drive means moves said front plunger away from and toward said rear plunger to establish and collapse said chamber.

9. Apparatus as in claim 1, wherein said space comprises a collapsible chamber of predetermined volume defined by opposing faces of said front and rear plungers and the inner wall of said bore when said plungers are within said bore in said predetermined spaced apart relationship to establish said chamber, said port is adapted to communicate with a source of liquid additive, and said drive means, with said plungers initially in their rearward positions in said bore in abutting relationship with said chamber collapsed and in communication with said port, moves said plungers apart to establish said chamber and fill the same with additive through said port, then reciprocates said plungers forwardly with said additive filled chamber therebetween to move said front plunger out of said bore and place said chamber in communication with the vessel interior, then moves said plungers together into abutting relationship to collapse said chamber and eject the additive therefrom and into the vessel, and then reciprocates said plungers rearwardly to move said front plunger into said bore and return said collapsed chamber into communication with said port, whereby said apparatus operates as a metering pump to inject a predetermined volume of the additive into the vessel.

10. Apparatus as in claim 9, wherein said drive means moves said front plunger away from and toward said rear plunger to establish and collapse said chamber.

11. Apparatus adapted to be mounted on a vessel containing a liquid, said apparatus comprising a housing having a bore for communication at a forward end with the interior of the vessel; liquid conveying means including a collapsible chamber of predetermined volume; means for reciprocating said liquid conveying means between a first position whereat said chamber projects from said forward end of said bore and is exposed to liquid in the vessel and a second position whereat said chamber is withdrawn into said bore in communication with a port therein; said chamber of predetermined volume being defined by the inner wall of said bore when said liquid conveying means is reciprocated to said second position, by the face of the end of a tubular member reciprocably mounted in said bore, by an opposed face of a piston mounted on a piston rod reciprocably mounted in said tubular member and extending therethrough, and by said piston rod extending between said opposed faces of said tubular member and piston; and said means for reciprocating including drive means operatively connected to each of said tubular member and piston for moving the same between a predetermined space apart relationship to establish said chamber of predetermined volume therebetween and a face-to-face abutting relationship to collapse said chamber, and for independently reciprocating each of said tubular member and piston forwardly and rearwardly.

12. Apparatus as in claim 11, wherein said drive means comprises first and second motor means respectively operatively connected to said tubular member and said piston for independently reciprocating the same forwardly and rearwardly and for moving the same between said abutting and spaced apart relationships.

13. Apparatus as in claim 12, wherein said first and second motor means comprise first and second pneumatic drive means.

14. Apparatus as in claim 13, wherein each said pneumatic drive means comprises a piston in an associated cylinder passage having a pair of inlet ports, one for receiving fluid under pressure to operate the pneumatic drive means to move its associated tubular member or piston forwardly and the other for receiving fluid under pressure to operate the pneumatic drive means to move its associated tubular member or piston rearwardly.

15. Apparatus as in claim 11, wherein said drive means reciprocates said tubular member and piston forwardly to said first position such that said chamber is established at said first position for being filled with liquid from the vessel, then reciprocates said tubular member and piston rearwardly, with said liquid filled chamber therebetween, to said second position whereat said chamber is in communication with said port, and then moves said tubular member and piston into abutting relationship to collapse said chamber and eject the liquid therein through said port under positive pressure, whereby said apparatus obtains a liquid sample of predetermined volume from the vessel and conveys the sample to and through the port.

16. Apparatus as in claim 15, wherein said drive means reciprocates said tubular member and piston forwardly in said face-to-face abutting relationship to initially place said chamber in communication with the vessel interior while said chamber is collapsed, and then moves said tubular member and piston to said spaced apart relationship to establish said chamber while said chamber is in communication with the vessel interior and prior to reciprocating said tubular member and piston rearwardly to said second position, whereby said chamber does not carry gas or liquid from the region of said port to the vessel interior and contamination of the liquid in the vessel is minimized.

17. Apparatus as in claim 11, wherein said port is adapted to communicate with a liquid additive, and said drive means, with said tubular member and piston initially in said second position in abutting relationship with said chamber collapsed, moves said tubular member and piston to said spaced apart relationship to establish said chamber and fill the same with additive through said port, then reciprocates said tubular member and piston forwardly with said additive filled chamber therebetween to place said chamber into communication with the vessel interior, then moves said tubular member and piston into said abutting relationship to collapse said chamber and eject the additive therefrom into the vessel, and then reciprocates said tubular member and piston rearwardly, with said collapsed chamber therebetween, to said second position, whereby said apparatus operates as a metering pump to inject a predetermined volume of additive into the vessel.

* * * * *